(12) United States Patent
Davies et al.

(10) Patent No.: US 10,575,819 B2
(45) Date of Patent: Mar. 3, 2020

(54) ROTATIONAL INTRAVASCULAR ULTRASOUND PROBE

(71) Applicant: Volcano Corporation, San Diego, CA (US)

(72) Inventors: Stephen Charles Davies, Ed Dorado Hills, CA (US); Norman Hugh Hossack, Folsom, CA (US); Peter Howard Smith, Sacramento, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 931 days.

(21) Appl. No.: 13/919,797

(22) Filed: Jun. 17, 2013

(65) Prior Publication Data

US 2013/0281864 A1   Oct. 24, 2013

Related U.S. Application Data

(63) Continuation of application No. 12/339,477, filed on Dec. 19, 2008, now Pat. No. 8,465,686.

(51) Int. Cl.
*A61B 8/00* (2006.01)
*A61B 5/00* (2006.01)
(Continued)

(52) U.S. Cl.
CPC ............ *A61B 8/445* (2013.01); *A61B 5/0084* (2013.01); *A61B 5/0095* (2013.01);
(Continued)

(58) Field of Classification Search
CPC ..... A61B 8/445; A61B 5/0066; A61B 5/0084; A61B 5/0095; A61B 8/0891; A61B 8/12;
(Continued)

(56) References Cited

U.S. PATENT DOCUMENTS

| 4,674,515 A | 6/1987 | Andou et al. |
| 4,748,985 A | 6/1988 | Nagasaki |

(Continued)

FOREIGN PATENT DOCUMENTS

| EP | 0754430 | 1/1997 |
| JP | 61-103436 | 5/1986 |

(Continued)

OTHER PUBLICATIONS

Japanese Patent Office, Japanese Office Action dated Sep. 1, 2015, Application No. 2011-554100. Translation included 2 pages.

(Continued)

*Primary Examiner* — Amanda Lauritzen Moher

(57) ABSTRACT

A rotational intravascular ultrasound probe for insertion into a vasculature and a method of manufacturing the same. The rotational intravascular ultrasound probe comprises an elongate catheter having a flexible body and an elongate transducer shaft disposed within the flexible body. The transducer shaft comprises a proximal end portion, a distal end portion, a drive shaft extending from the proximal end portion to the distal end portion, an ultrasonic transducer disposed near the distal end portion for obtaining a circumferential image through rotation, and a transducer housing molded to the drive shaft and the ultrasonic transducer.

19 Claims, 9 Drawing Sheets

(51) Int. Cl.
*A61B 8/12* (2006.01)
*A61B 8/08* (2006.01)
*B29C 45/00* (2006.01)
*B29C 45/14* (2006.01)

(52) U.S. Cl.
CPC .............. *A61B 8/0891* (2013.01); *A61B 8/12* (2013.01); *A61B 8/44* (2013.01); *A61B 8/4444* (2013.01); *A61B 8/4455* (2013.01); *A61B 8/4461* (2013.01); *A61B 8/4483* (2013.01); *A61B 8/4494* (2013.01); *B29C 45/0053* (2013.01); *B29C 45/14549* (2013.01); *A61B 5/0066* (2013.01); *A61B 8/08* (2013.01); *A61B 8/085* (2013.01); *A61B 8/0833* (2013.01); *Y10T 29/49005* (2015.01)

(58) Field of Classification Search
CPC ... A61B 8/4444; A61B 8/4461; A61B 8/4494; A61B 8/4483; A61B 8/4455; A61B 8/44; A61B 8/085; A61B 8/0833; A61B 8/08; B29C 45/0053; B29C 45/14549; Y10T 29/49005
USPC .................. 600/459, 462, 466, 467
See application file for complete search history.

(56) References Cited

U.S. PATENT DOCUMENTS

| | | | |
|---|---|---|---|
| 4,763,663 A | 8/1988 | Uphold et al. | |
| 4,803,992 A | 2/1989 | Lemelson | |
| 5,115,809 A | 5/1992 | Saitoh et al. | |
| 5,115,814 A * | 5/1992 | Griffith | A61B 5/06 600/439 |
| 5,176,140 A | 1/1993 | Kami et al. | |
| 5,209,235 A | 5/1993 | Briken et al. | |
| 5,271,402 A | 12/1993 | Yeung et al. | |
| 5,313,950 A | 5/1994 | Ishikawa et al. | |
| 5,485,846 A | 1/1996 | Webler et al. | |
| 5,596,991 A | 1/1997 | Tanaka | |
| 5,810,009 A | 9/1998 | Mine et al. | |
| 5,810,733 A | 9/1998 | Van Creveld et al. | |
| 5,827,313 A | 10/1998 | Ream | |
| 5,846,205 A | 12/1998 | Curley et al. | |
| 6,004,273 A | 12/1999 | Sakamoto et al. | |
| 6,017,311 A | 1/2000 | Sakamoto | |
| 6,017,312 A | 1/2000 | Masters | |
| 6,110,121 A * | 8/2000 | Lenker | A61B 8/12 600/463 |
| 6,149,599 A | 11/2000 | Schlesinger et al. | |
| 6,325,760 B1 | 12/2001 | Takanori et al. | |
| 6,709,396 B2 | 3/2004 | Flesch et al. | |
| 6,709,397 B2 | 3/2004 | Taylor | |
| 6,758,818 B2 | 7/2004 | Pantages et al. | |
| 7,396,332 B2 | 7/2008 | Taimisto et al. | |
| 8,465,686 B2 * | 6/2013 | Davies | A61B 5/0084 264/272.14 |
| 2001/0021811 A1 * | 9/2001 | Yock | A61B 5/02007 600/466 |
| 2002/0007120 A1 * | 1/2002 | Moore | A61B 8/12 600/466 |
| 2002/0103448 A1 * | 8/2002 | Babaev | A61N 7/00 601/2 |
| 2002/0156379 A1 * | 10/2002 | Angelsen | B06B 1/0614 600/459 |
| 2003/0060737 A1 * | 3/2003 | Brisken | A61N 7/022 601/2 |
| 2003/0100834 A1 | 5/2003 | Umeda et al. | |
| 2003/0208119 A1 | 11/2003 | Crowley | |
| 2004/0199047 A1 | 10/2004 | Taimisto | |
| 2005/0027198 A1 * | 2/2005 | Couvillon, Jr. | A61B 8/12 600/466 |
| 2006/0173337 A1 | 8/2006 | Chen et al. | |
| 2006/0173350 A1 | 8/2006 | Yuan et al. | |
| 2007/0038110 A1 * | 2/2007 | Flesch | A61B 8/12 600/459 |
| 2007/0078345 A1 * | 4/2007 | Mo | A61B 8/12 600/459 |
| 2007/0167813 A1 | 7/2007 | Lee et al. | |
| 2007/0178768 A1 | 8/2007 | Harshman et al. | |
| 2007/0244391 A1 * | 10/2007 | Hirota | A61B 5/0066 600/443 |
| 2008/0161696 A1 | 7/2008 | Schmitt et al. | |
| 2008/0177183 A1 | 7/2008 | Courtney et al. | |
| 2009/0221958 A1 | 9/2009 | Beyar et al. | |
| 2016/0058414 A1 * | 3/2016 | Corl | A61B 8/4494 600/463 |

FOREIGN PATENT DOCUMENTS

| | | |
|---|---|---|
| JP | 08-191835 | 7/1996 |
| JP | 2001-327502 | 11/2001 |
| JP | 2002501809 A | 1/2002 |
| JP | 2002501809 A | 1/2002 |
| JP | 2008526437 | 7/2008 |
| JP | 2008526437 A | 7/2008 |
| WO | WO 99/39640 | 8/1999 |
| WO | WO 031103501 | 12/2003 |
| WO | WO 2006/076428 A1 | 7/2006 |
| WO | WO 08/086613 | 7/2008 |
| WO | WO2008/086356 | 7/2008 |
| WO | WO 2008/086356 A2 | 7/2008 |

OTHER PUBLICATIONS

Supplementary European Search Report received in European Patent Application No. 10751228.7, dated Feb. 18, 2013, 8 pages.
Japanese Office Action and translation received in Japanese Application No. 2011-542485, dated Jan. 15, 2014, 4 pages. Dated Jan. 10, 2014.
Japanese Office Action and English Translation received in Japanese Application No. 2011-554100, dated Jan. 14, 2014, 7 pages.
International Searching Authority/Korean Intellectual Property Office, "International Search Report of the International Searching Authority," for PCT/US2009/068724, dated Jul. 20, 2010, 3 pages.
International Searching Authority/Korean Intellectual Property Office, "Notification of Transmittal of the International Search Report and The Written Opinion of the international Searching Authority, or the Declaration," for PCT/US2010/026491, dated Sep. 28, 2010, 8 pages.
Supplementary European Search Report received in European Patent Application No. 09837983.6, dated Apr. 4, 2013; 9 pages.
European Patent Office, "Examination Report" for Application No. 10751228.7, dated Sep. 29, 2016, 7 pages.

* cited by examiner

ROTATIONAL INTRAVASCULAR ULTRASOUND PROBE

BACKGROUND

Intravascular Ultrasound (IVUS) has become an important interventional diagnostic procedure for imaging atherosclerosis and other vessel diseases and defects. In the procedure, an IVUS catheter is threaded over a guidewire into a blood vessel of interest, and images are acquired of the atherosclerotic plaque and surrounding area using ultrasonic echoes. This information is much more descriptive than the traditional standard of angiography, which only shows an image of the blood flowing through the vessel lumen. Some of the key applications of IVUS include: determining a correct diameter and length of a stent to choose for dilating an arterial stenosis, verifying that a post-stenting diameter and luminal cross-section area are adequate, verifying that a stent is well apposed against a vessel wall to minimize thrombosis and optimize drug delivery (in the case of a drug eluting stent) and identifying an exact location of side-branch vessels. In addition, new techniques such as virtual histology (RF signal-based tissue characterization) show promise of aiding identification of vulnerable plaque (i.e., plaque which is prone to rupture and lead to onset of a heart attack).

There are generally two standard types of IVUS catheters: mechanical/rotational IVUS catheters and solid state catheters. In a rotational IVUS catheter, a single transducer consisting of a piezoelectric crystal is rotated at approximately 1800 revolutions per minute while the element is excited by a signal. This excitation causes the element to vibrate at a frequency dependant upon its thickness, which depending on the dimensions and characteristics of the transducer this can be from around 9 to 45 MHz. The single element transducer of the rotational IVUS catheter can be made very thin and therefore able to vibrate at relatively high frequencies, thus achieving a relatively high resolution, this is of particular value in the near field (close to the outside diameter of the catheter sheath). In addition, this type of catheter configuration facilitates the use of relatively high excitation voltages, increasing the signal to noise ratio.

In rotational IVUS catheters, the transducer subassembly is situated in a preformed metallic structure called a transducer housing that is attached via adhesive or weld to an end of the drive cable. The metallic transducer housing is often formed with stainless steel. A backing material is formed from a loaded liquid two-part epoxy that is applied to the back side of the transducer subassembly when the transducer subassembly is inserted into the transducer housing. The backing material is then cured to couple the transducer subassembly to the preformed metallic housing.

The preformed metallic housing can negatively impact image quality because it is constructed of a strongly reflective and resonant material. In addition, the transducer subassembly and transducer housing are usually very small, which makes reliable and consistent manufacture within small tolerances difficult. Secure and precise placement of the transducer subassembly within the preformed transducer housing can also be difficult.

BRIEF SUMMARY

A rotational intravascular ultrasound probe is disclosed herein for insertion into a body cavity, such as a blood vessel. The probe comprises an elongate flexible catheter body surrounding a transducer shaft having an ultrasonic transducer, a transducer housing, and a drive shaft. The drive shaft has a proximal end portion and a distal end portion. The transducer housing is molded to the transducer and the drive shaft near the distal end. The transducer is positioned such that ultrasonic waves are transmitted from and received on a surface of the transducer.

In a disclosed embodiment, the rotational intravascular ultrasound probe comprises an elongate catheter having a flexible body and an elongate transducer shaft disposed within the flexible body. The transducer shaft comprises a proximal end portion, a distal end portion, a drive shaft extending from the proximal end portion to the distal end portion, an ultrasonic transducer disposed near the distal end portion for obtaining a circumferential image through rotation, and a transducer housing molded to the drive shaft and the ultrasonic transducer.

Furthermore, an embodiment of a method of manufacturing a rotational intravascular ultrasound probe is disclosed. The method comprises providing an injection mold having a recess, providing an ultrasonic transducer for obtaining a circumferential image through rotation, the transducer being coupled to a wire, disposing the transducer within the recess, placing a drive cable over the wire, and injecting a material into the injection mold to form a transducer housing attached to the transducer and the drive cable.

DETAILED DESCRIPTION

Figure 1:
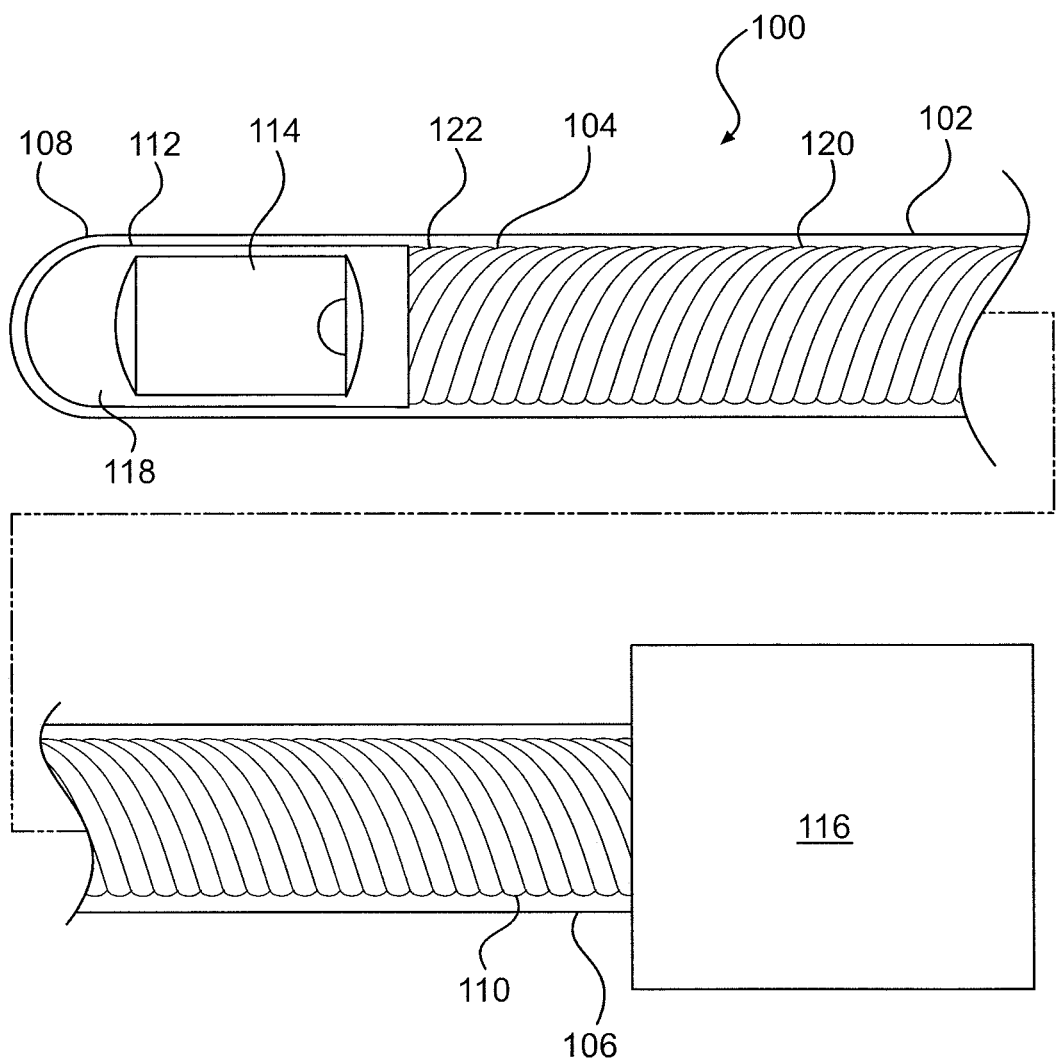
FIG. 1 is a fragmentary view of a rotational IVUS probe having a transducer shaft with a molded transducer housing.

Turning to the figures, representative illustrations of the rotational intravascular ultrasound (IVUS) probe having a molded transducer housing and a method of molding the same are shown therein. Referring specifically to FIG. 1, a rotational intravascular ultrasound (IVUS) probe 100 for insertion into a patient for diagnostic imaging is shown. The probe 100 comprises a catheter body 102 and a transducer shaft 104. The catheter body 102 is flexible and has both a proximal end portion 106 and a distal end portion 108. The catheter body 102 is a sheath surrounding the transducer shaft 104. For explanatory purposes, the catheter body 102 in FIG. 1 is illustrated as visually transparent such that the transducer shaft 104 disposed therein can be seen, although it will be appreciated that the catheter body 102 may or may not be visually transparent. The transducer shaft 104 is flushed with a sterile fluid, such as saline, within the catheter body 102. The fluid serves to eliminate the presence of air pockets around the transducer shaft 104 that adversely affect image quality. The fluid can also act as a lubricant. The transducer shaft 104 has a proximal end portion 110 disposed within the proximal end portion 106 of the catheter body 102 and a distal end portion 112 disposed within the distal end portion 108 of the catheter body 102.

The distal end portion 108 of the catheter body 102 and the distal end portion 112 of the transducer shaft 104 are inserted into a patient during the operation of the probe 100. The usable length of the probe 100 (the portion that can be inserted into a patient) can be any suitable length and can be varied depending upon the application. The distal end portion 112 of the transducer shaft 104 includes a transducer subassembly 114, which is described in further detail below.

The proximal end portion 106 of the catheter body 102 and the proximal end portion 110 of the transducer shaft 104 are connected to an interface module 116 (sometimes referred to as a patient interface module or PIM). The proximal end portions 106, 110 are fitted with a connector, which is received by a complimentary connector on the interface module 116. The rotation of the transducer shaft 104 within the catheter body 102 is controlled by the interface module 116, which provides a plurality of user interface controls that can be manipulated by a user. The interface module 116 also communicates with the transducer subassembly 114 by sending and receiving electrical signals to and from the transducer subassembly 114 via wires within the transducer shaft 104. The interface module 116 can receive, analyze, and display information received through the transducer shaft 104. It will be appreciated that any suitable functionality, controls, information processing and analysis, and display can be incorporated into the interface module 116.

Figure 2:
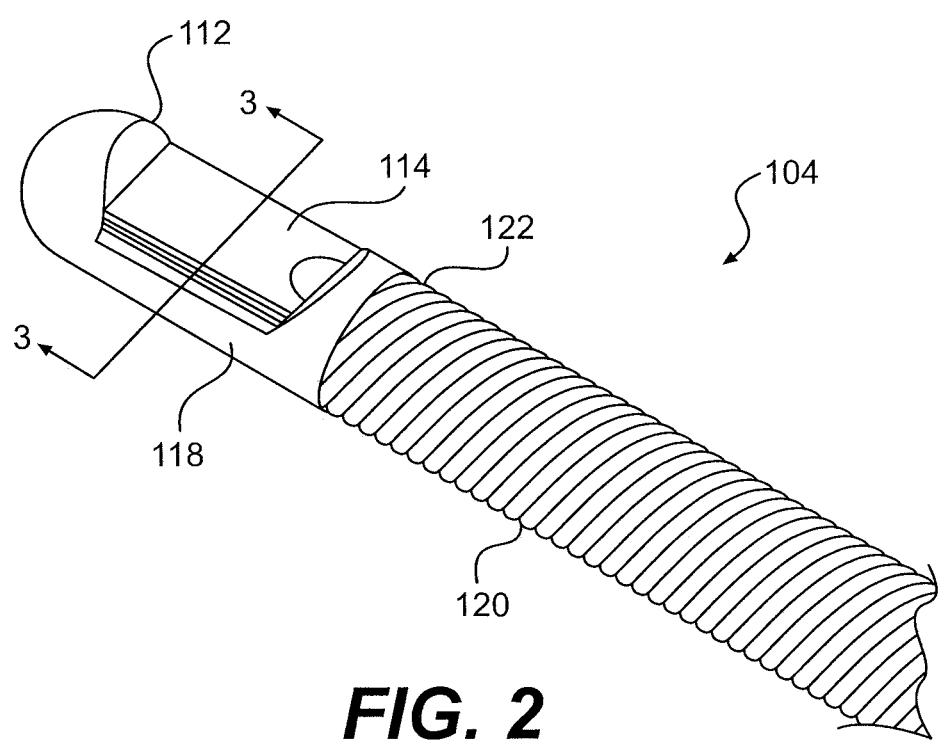
FIG. 2 is a fragmentary perspective view of the transducer shaft for the rotational IVUS probe of FIG. 1.

FIG. 2 shows the transducer shaft 104 independent from the catheter body 102 for purposes of discussion. The transducer shaft 104 includes a transducer subassembly 114, a transducer housing 118, and a drive cable 120. The transducer subassembly 114 is coupled to the transducer housing 118. The illustrated transducer subassembly 114 is a single transducer subassembly 114 having a single transducer. The transducer housing 118 is attached to the drive cable 120 near a distal end 122 of the drive cable 120. The drive cable 120 is rotated within the catheter body 102 via the interface module 116 to rotate the transducer housing 118 and the transducer subassembly 114.

The transducer subassembly 114 can be of any suitable type and can include any suitable number of layers. As an example, referring to FIG. 3, the transducer subassembly 114 can include a front matching layer 124, a first electrode layer 126, a transducer layer 128, a second electrode layer 130, and a back matching layer 132. Each layer may be formed from any suitable material. For example, the transducer layer 128 may be formed with any suitable material, including but not limited to a piezoelectric material such as PZT (lead zirconate titanate). As another example, the electrode layers 126, 130 may be formed with any suitable conductive material, including but not limited to gold. The matching layers 124, 132 may be formed with any suitable material, including but not limited to materials having a relatively high acoustic impedance such as loaded plastic or epoxy.

Referring again to FIG. 2, the transducer housing 118 is integrally molded to the transducer subassembly 114 and drive cable 120. Utilizing a molded transducer housing 118 provides a transducer shaft 104 that can be repeatedly manufactured with precise and accurate placement of the transducer subassembly 114 with respect to the drive cable 120. The scalability of the transducer housing 118 is enhanced because it is easier and more efficient to reliably mold the transducer housing 118 around smaller transducer subassemblies. In addition, the transducer housing 118 offers significant mechanical support and protection to the transducer subassembly 114 during rotation.

The molded transducer housing 118 may be formed with any suitable material. In certain embodiments, the molded transducer housing 118 is molded using a material (sometimes referred to as a backing material) that can offer certain advantages to the operation of the probe 100. For example, unlike a metallic housing, which creates a strongly reflective and resonant structure, the transducer housing 118 can be molded using a material having more favorable characteristics. As an example, the material can have a relatively high acoustic impedance and attenuation to contribute to an improvement in image quality. In some embodiments, it is desirable for the transducer housing 118 to be rigid such that the transducer subassembly 114 can be securely retained, protected, and consistently directed in the desired circumferential direction as the transducer shaft 104 is rotating. By way of example and not limitation, the material forming the molded transducer housing 118 can include a loaded liquid two-part epoxy such as Master Bond EP30M or Bondline Silver.

The transducer housing 118 may comprise one or more materials disposed therein. These materials can act as scatterers and/or absorbers. In certain embodiments, one or more particles of a metal oxide, such as Cerium Oxide, can be embedded in the transducer housing material to raise both the density and acoustic velocity of the material as well as improve its ability to attenuate ultrasound. In some embodiments, hollow microspheres can be added to the transducer housing material to scatter errant ultrasound energy. Other structures can be disposed within the transducer housing material. For example, shaped electron-dense features can be molded within the transducer housing 118 to facilitate identification of device orientation on fluoroscopic images. In addition, the density of the transducer housing material can be adjusted to affect the visualization of the transducer housing 118 under fluoroscopy. The greater the electron density, the darker the appearance of the transducer housing 118 when viewed under fluoroscopy.

In some embodiments, the transducer housing 118 has channels or receptacles molded therein for the delivery and/or transport of fluids or suspensions. By way of example, the molded transducer housing 118 can be used to deliver drugs, such a anticoagulants, to the patient. The molded transducer housing 118 could also be used to draw fluid disposed near the housing.

It will be appreciated that any suitable mold may be used to form the molded transducer housing 118. As an example, the molded transducer housing 118 can be formed utilizing a mold such as the injection mold 134 shown in FIGS. 4 and 5. The injection mold 134 has a first mold plate 136 and a second mold plate 138. The first mold plate 136 can be disposed below the second mold plate 138. The two mold plates 136, 138 can be brought together and mated to create one or more cavities for receiving portions of the transducer shaft 104 and receiving the material injected into the mold to form the transducer housing 118. The mold can also have injection ports, such as injection port 140, and vent ports, such as vent port 142, as needed for the molding process.

Figure 6:
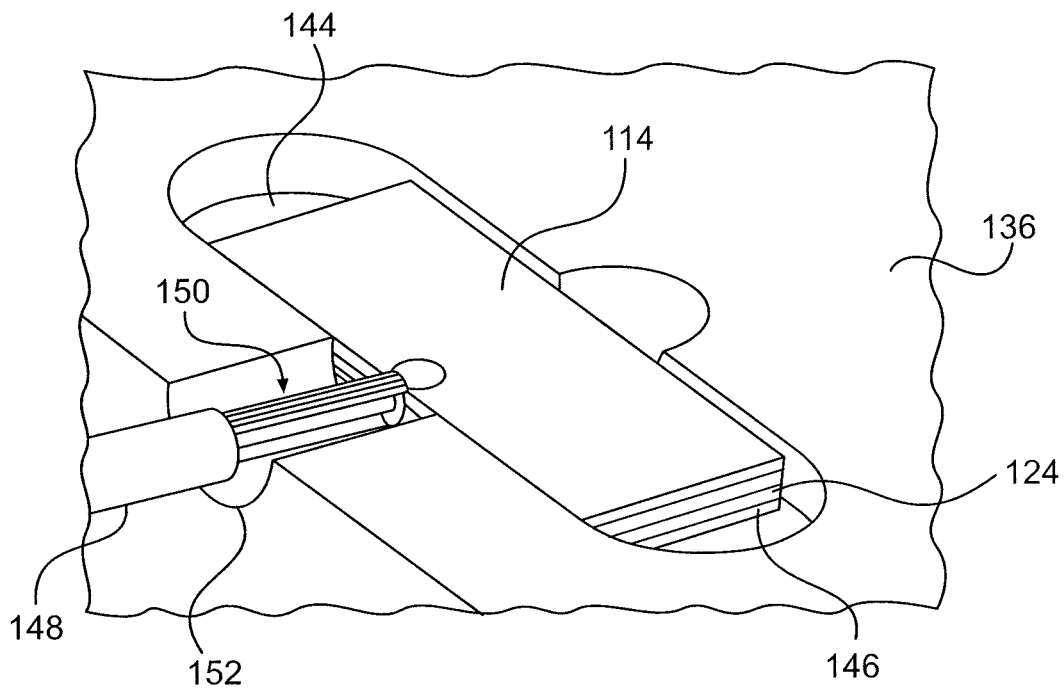
FIG. 6 is a fragmentary perspective view of the transducer shaft of FIG. 2 disposed within the mold of FIG. 4.

By way of example and not limitation, the molding of the transducer housing 118 may be accomplished as generally shown in FIGS. 6-10. Referring to FIG. 6, a suitable transducer subassembly 114 is provided and disposed within a mold cavity 144 in the first mold plate 136. As illustrated, the transducer subassembly 114 is oversized to facilitate accurate placement of the transducer subassembly 114 within the mold cavity 144. The mold cavity 144 is correspondingly sized to receive the oversized transducer subassembly 114 such that transducer subassemblies can be repeatedly and reliably placed into the first mold plate 136 during mass production. In this way, transducer housings 118 can be consistently molded to maintain a desired distance between the transducer subassembly 114 and the drive cable 120.

As shown in FIGS. 6-9, the transducer subassembly 114 has a removable sacrificial layer 146 disposed over the front of the transducer subassembly 114 to cover the front surface of the transducer subassembly, which is the front matching layer 124 in this embodiment. The sacrificial layer 146 protects the transducer subassembly 114 prior to and during the process of molding the transducer housing 118. The sacrificial layer 146 is later removed from the transducer subassembly 114 as described further below.

Prior to placing the transducer subassembly 114 within the mold cavity 144, as shown in FIG. 6, the transducer subassembly 114 is coupled to a cable 148 including a plurality of electrical wires 150 conductively connected to the transducer subassembly 114 to receive and send signals between the transducer subassembly 114 and the interface module 116. The cable 148 is received within a cable cavity 152 of the mold 134 when the transducer subassembly 114 is inserted into the mold 134.

Figure 4:
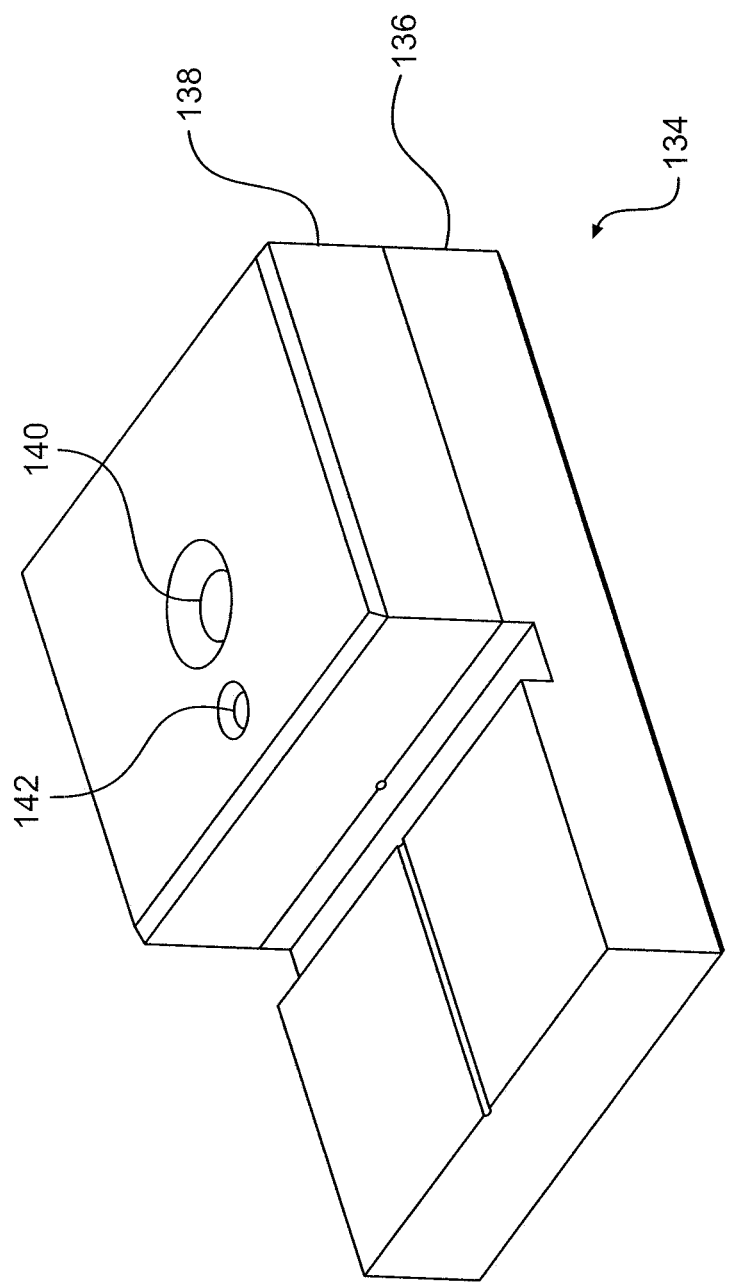
FIG. 4 is a perspective view of a mold for forming the molded transducer housing for the transducer shaft of FIG. 2.
Figure 5:
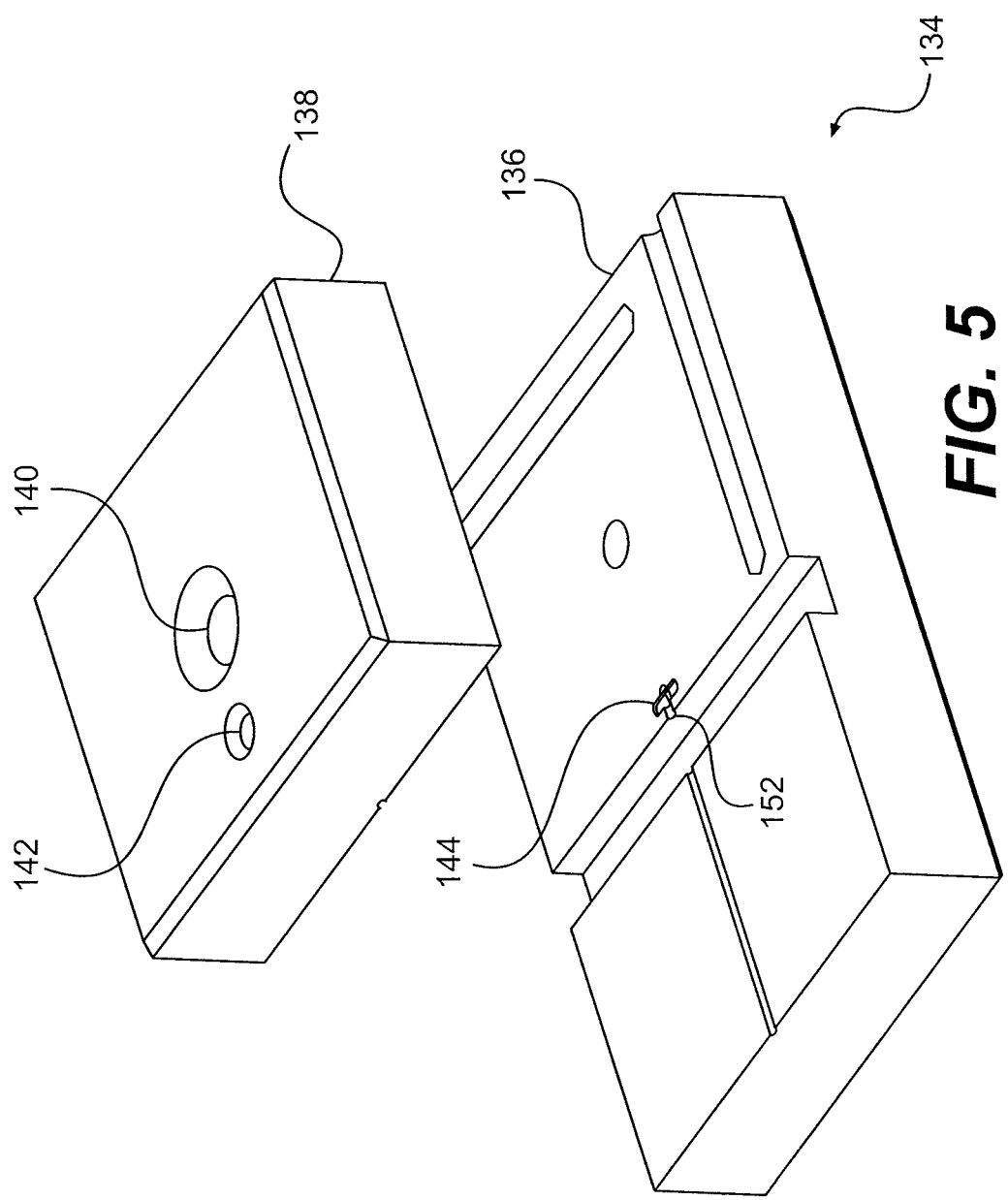
FIG. 5 is an exploded perspective view of the mold of FIG. 4.
Figure 7:
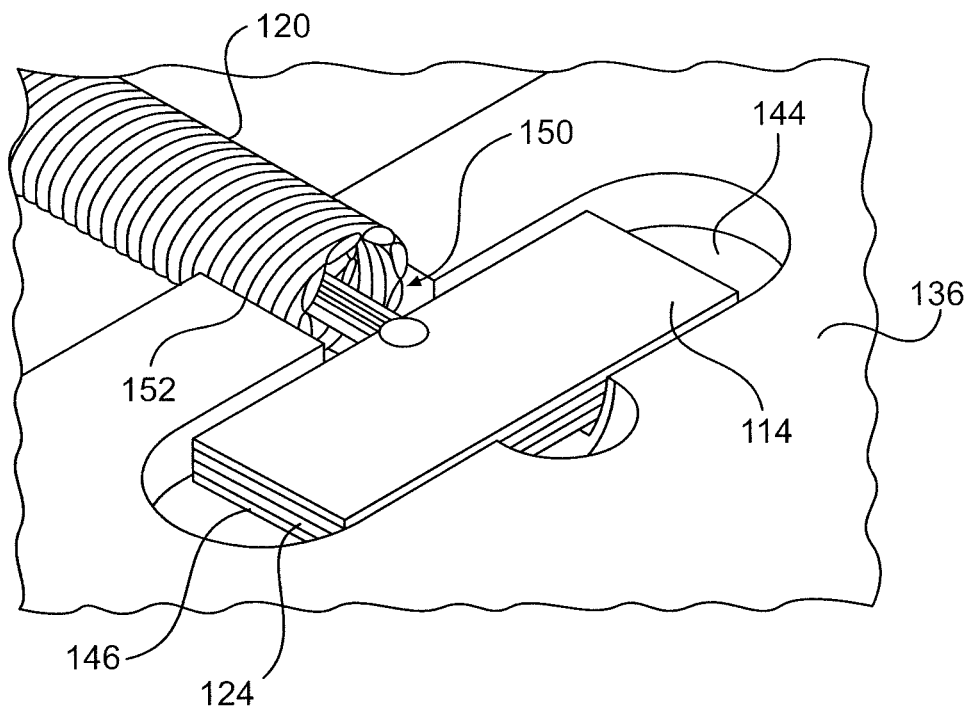
FIG. 7 is another fragmentary perspective view of the transducer shaft of FIG. 2 disposed within the mold of FIG. 4 and showing a drive cable inserted into the mold.
Figure 8:
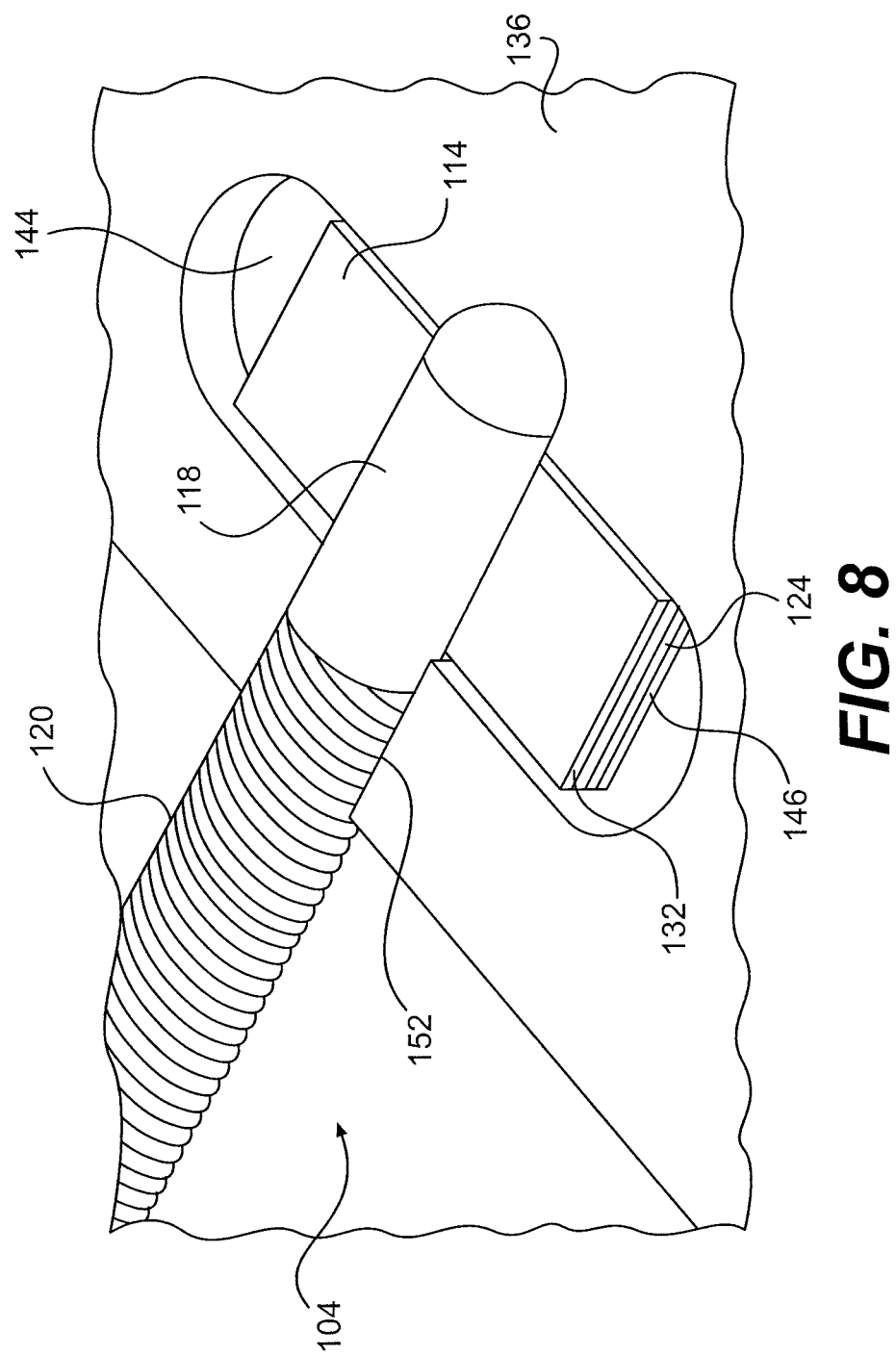
FIG. 8 is another fragmentary perspective view of the transducer shaft of FIG. 2 disposed within the mold of FIG. 4 showing the molded transducer housing after formation in the mold.

Turning to FIG. 7, the drive cable 120 is moved over the cable 148 such that it is positioned near the transducer subassembly 114 in the mold 134. The drive cable 120 surrounds and protects the cable 148 during operation of the probe 100. Once the transducer subassembly 114, the cable 148, and the drive cable 120 are disposed within the mold 134, the first and second mold plates 136, 138 are combined such as shown in FIG. 4, and the material forming the transducer housing 118 is injected into the mold 134 and cured. The first and second mold plates 136, 138 are then separated from one another, thus leaving the transducer shaft 104 in the mold cavity 144 of the first mold plate 136 as shown in FIG. 8. Through this process, the transducer housing 118 is formed in a single molding step.

Figure 3:
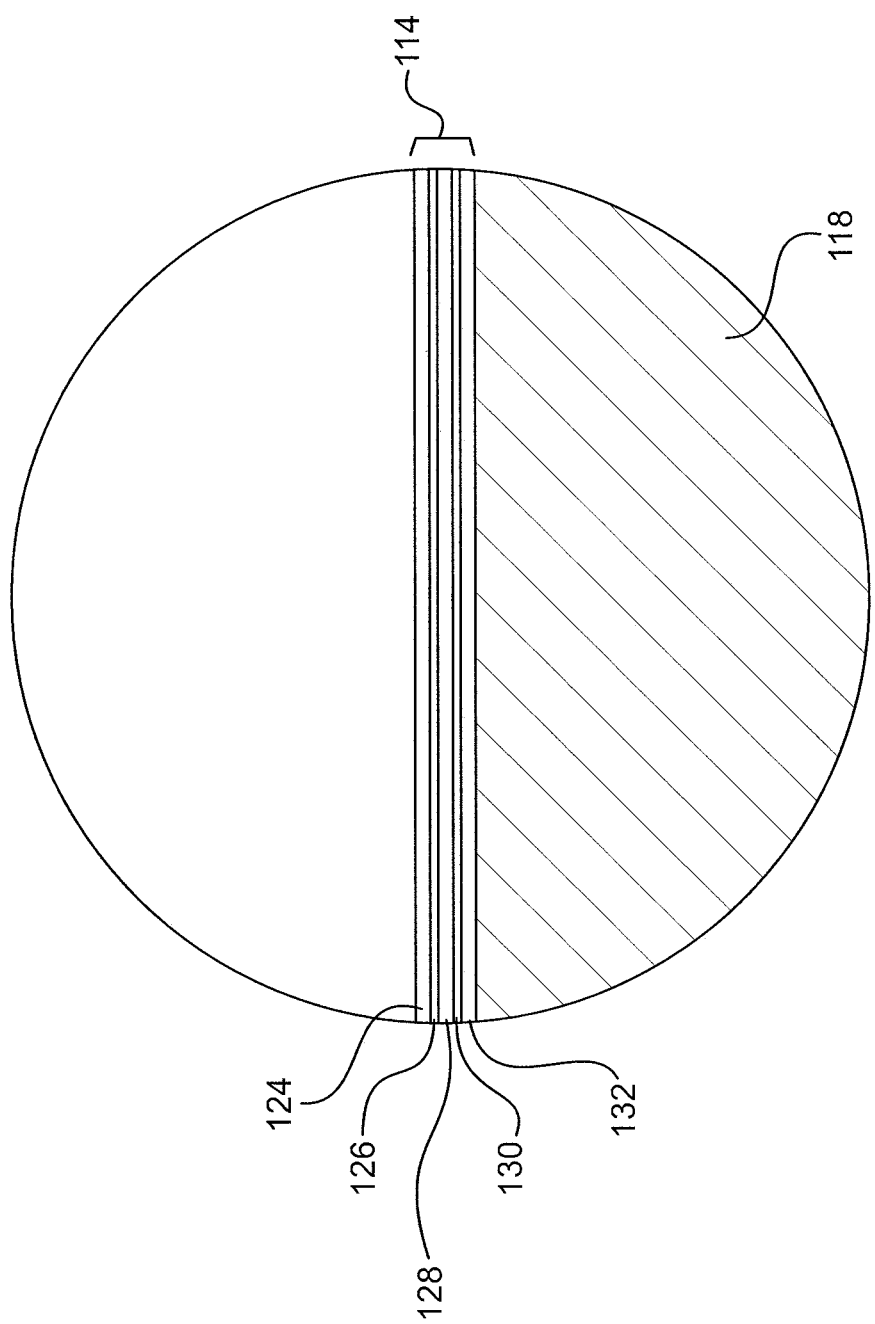
FIG. 3 is an enlarged section view of the transducer shaft taken through line 3-3 of FIG. 2.

The transducer housing 118 is molded over the back matching layer 132, as shown in FIG. 3, and to the drive cable 120, as shown in FIG. 8. The portions of the electrical wires 150 extending between the drive cable 120 and the transducer subassembly 114 are molded within the transducer housing 118. Referring to FIGS. 2 and 8, in the illustrated example, the transducer housing 118 is generally cylindrical with a domed end. As shown, the transducer housing 118 is linear in shape to facilitate the rapid rotation of the transducer shaft 104. In addition, the front surface of the transducer subassembly 114 is oriented in a plane that is generally perpendicular to a plane extending radially from the rotational axis of the transducer shaft 104 through the center of the transducer subassembly 114. In some embodiments, the transducer housing 118 can be molded to position the transducer subassembly 114 in other suitable orientations. For example, the transducer housing 118 can be molded such that the front surface of the transducer subassembly 114 can be oriented in a plane that is approximately 30°, 45°, or 60° relative to a plane extending radially from the rotational axis of the transducer shaft 104 through the center of the transducer subassembly 114. It will be appreciated that the transducer housing 118 can have any suitable shape and any suitable size. In addition, the transducer subassembly 114 can be oriented in any suitable manner.

Figure 9:
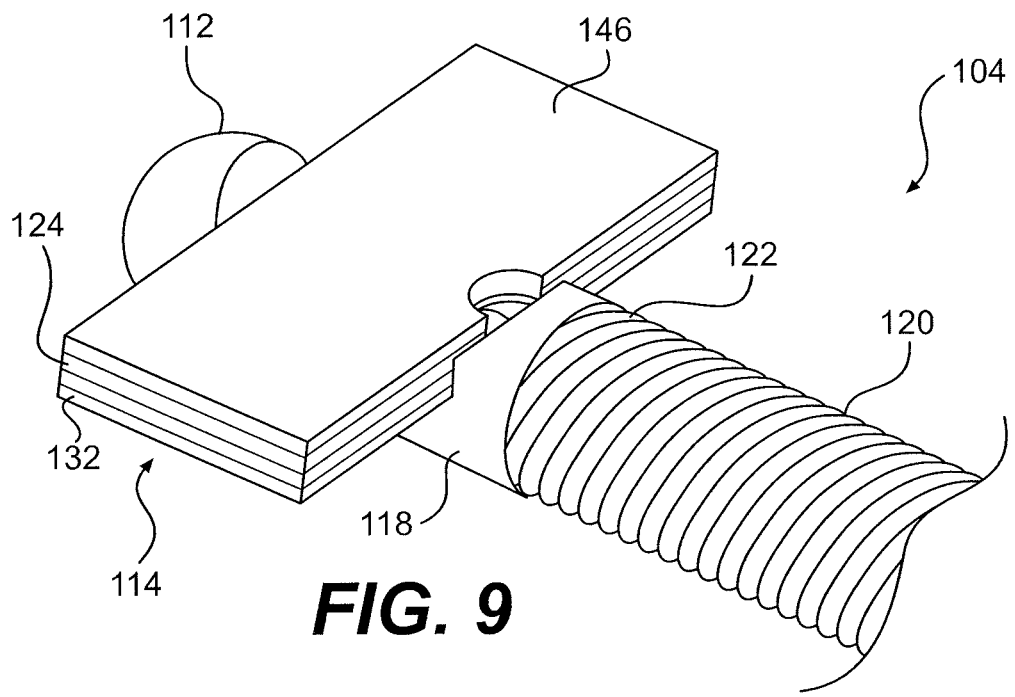
FIG. 9 is a fragmentary perspective view of the transducer shaft of FIG. 2 after removal from the mold of FIG. 4.
Figure 10:
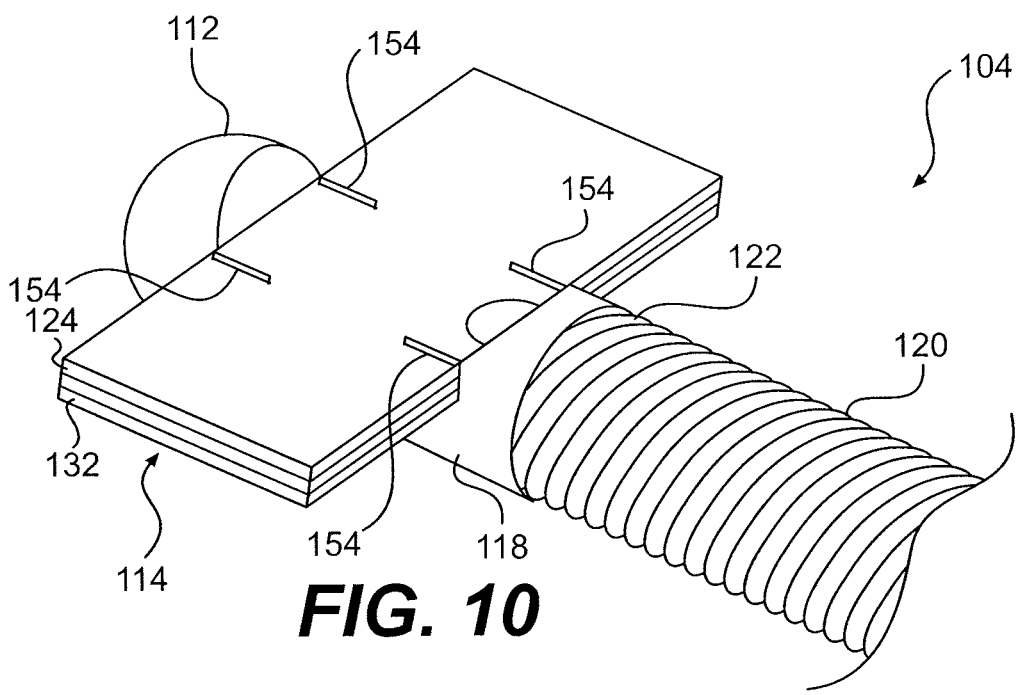
FIG. 10 is another fragmentary perspective view of the transducer shaft of FIG. 2 after removal from the mold of FIG. 4 and with a sacrificial layer removed from a transducer subassembly.

Turning to FIG. 9, the transducer shaft 104 is removed from the mold with the transducer housing 118 fully formed and the sacrificial layer 146 still attached. At this point, the sacrificial layer 146 has served its purpose of protecting the front surface of the transducer subassembly 114 during the molding process and can be removed as shown in FIG. 10.

Depending on the size of the oversized transducer subassembly 114, it may require trimming to allow for the transducer shaft 104 to rotate as desired within the catheter body 102. The transducer subassembly 114 may be trimmed, for example, by cutting each side of the transducer subassembly 114 at or near the outer periphery of the transducer housing 118 such as represented by fracture lines 154. The transducer subassembly 114 may be completely cut through the fracture lines 154, or alternatively, the fracture lines 154 may be formed and the transducer subassembly 114 can be broken along the fracture lines 154. In some embodiments, the transducer subassembly 114 can be ground to reduce its size. The transducer shaft 104 is thus produced, as shown in FIG. 2, such that it can be rotated to obtain a circumferential image of surrounding tissue during operation of the probe 100.

It is noted that transducer layer 128, as shown in FIG. 3, may be any suitable size. In some embodiments, the transducer subassembly 114 is very thin and can have a thickness on the order of approximately 50 micro meters. For purposes of explanation, the transducer subassembly 114 and other features of the probe 100 may be shown larger than scale in the figures.

Figure 11:
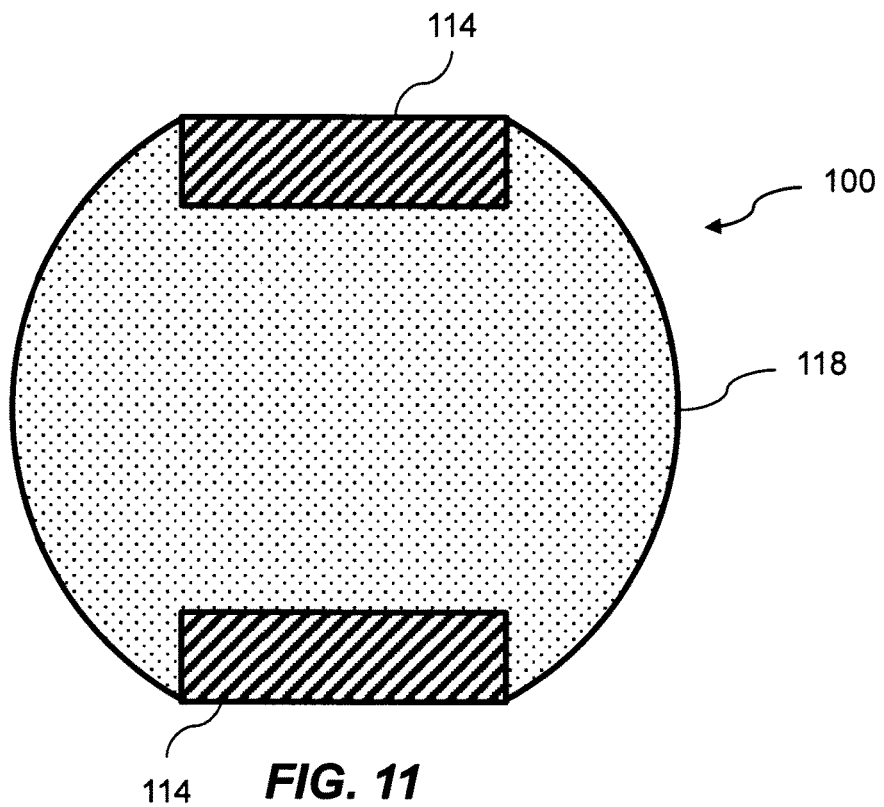
FIG. 11 illustrates an ultrasound probe including a transducer housing and two transducer subassemblies.
Figure 12:
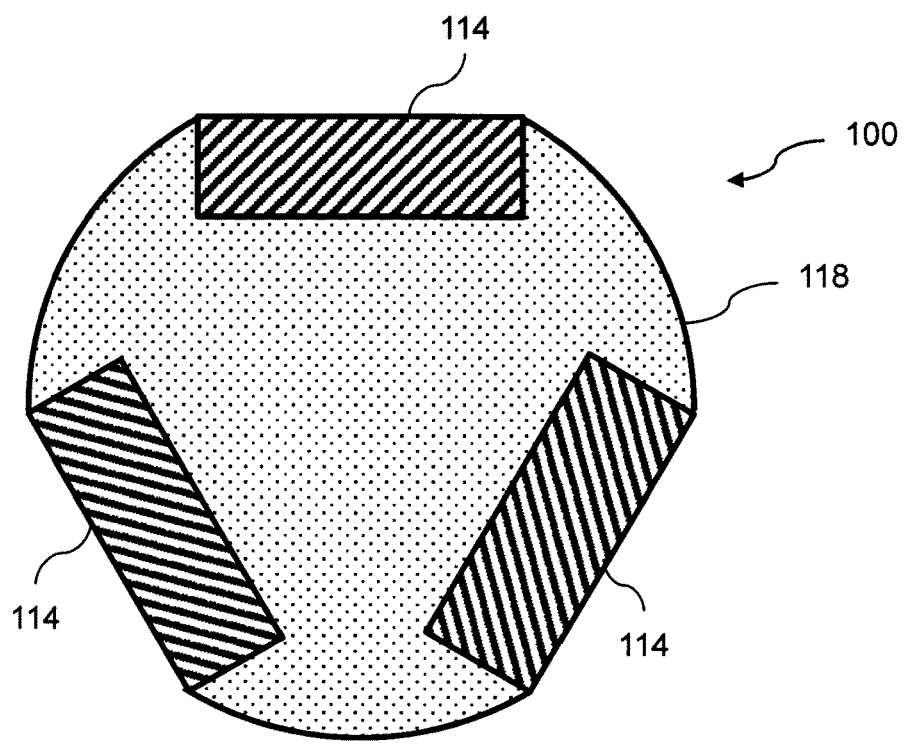
FIG. 12 illustrates an ultrasound probe including a transducer housing and three transducer subassemblies.

In some embodiments, the transducer shaft 104 can have more than one transducer subassembly 114. For example, the molded transducer housing 118 can have two diametrically opposed transducer subassemblies 114 as shown in FIG. 11. In another embodiment, the molded transducer housing 118 can have three transducer subassemblies 114 circumferentially positioned 120° from one another as shown in FIG. 12. Having more than one transducer subassembly 114 permits the probe 100 to operate at multiple frequencies to provide comprehensive information on the target tissue. Generally, lower frequencies can penetrate deeper into tissue, whereas higher frequencies can provide more information on tissue near the probe 100, such as plaque composition. Operating with more than one transducer subassembly 114 can also permit the transducer shaft 104 to be rotated at a lower speed.

In some embodiments, in addition to or in place of the transducer subassembly 114, the probe 100 can have a prism and lens configuration for the practice of optical coherence tomography or photo acoustic imaging.

Besides intravascular ultrasound, other types of ultrasound probes can be made using the teachings provided herein. By way of example and not limitation, other suitable types of probes include non-intravascular intraluminal ultrasound probes, intracardiac echo probes, laparoscopic, and interstitial probes. In addition, the probe 100 may be used in any suitable anatomy, including, but not limited to, coronary, carotid, neuro, peripheral, or venous. The scalability of the probe 100, accomplished via the molding process described herein, makes the probe 100 particularly useful for small vessel applications.

Recitation of ranges of values herein are merely intended to serve as a shorthand method of referring individually to each separate value falling within the range, unless otherwise indicated herein, and each separate value is incorporated into the specification as if it were individually recited herein.

Any references, including publications, patent applications, and patents, cited herein are hereby incorporated by reference to the same extent as if each reference were individually and specifically indicated to be incorporated by reference and were set forth in its entirety herein (including any references contained therein).

Illustrative embodiments of a mechanical rotational IVUS probe are described herein. Variations of the disclosed embodiments will be apparent to those of ordinary skill in the art in view of the foregoing illustrative examples. Those skilled in the relevant art will employ such variations as appropriate, and such variations, embodied in alternative embodiments, are contemplated within the scope of the disclosed invention. The invention is therefore not intended to be limited to the examples described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A rotational intravascular ultrasound probe for insertion into a vasculature, the probe comprising:
    an elongate catheter comprising a flexible body; and
    an elongate transducer shaft disposed within the flexible body, the transducer shaft comprising:
        a longitudinal axis;
        a proximal end portion and a distal end portion;
        a drive cable extending from the proximal end portion to the distal end portion of the elongate transducer shaft, the drive cable comprising a distal portion;
        an ultrasonic transducer for obtaining a circumferential image through rotation, the ultrasonic transducer disposed at the distal end portion, wherein the ultrasonic transducer comprises a stack of layers extending perpendicular to the longitudinal axis;
        a plurality of electrical wires passing through the drive cable to the ultrasonic transducer; and
        a transducer housing conforming to and physically contacting the distal portion of the drive cable, one or more layers of the stack of layers of the ultrasonic transducer, and the plurality of electrical wires.

2. The rotational intravascular ultrasound probe of claim 1 wherein the ultrasonic transducer comprises a single imaging element.

3. The rotational intravascular ultrasound probe of claim 1 wherein the transducer housing is rigid.

4. The rotational intravascular ultrasound probe of claim 1 wherein the transducer housing comprises an epoxy.

5. The rotational intravascular ultrasound probe of claim 1 wherein the ultrasonic transducer includes a piezoelectric material.

6. The rotational intravascular ultrasound probe of claim 1 wherein the transducer housing is cylindrically-shaped.

7. The rotational intravascular ultrasound probe of claim 1 wherein the transducer housing has a linear shape.

8. The rotational intravascular ultrasound probe of claim 1 wherein the transducer housing has a domed end.

9. The rotational intravascular ultrasound probe of claim 1 wherein the stack of layers of the ultrasonic transducer includes a front matching layer, a first electrode layer, a transducer layer, a second electrode layer, and a back matching layer, and wherein the transducer housing surrounds the ultrasonic transducer such that the transducer housing is in contact with at least the back matching layer.

10. The rotational intravascular ultrasound probe of claim 1 wherein the proximal end portion of the transducer shaft comprises a connector.

11. The rotational intravascular ultrasound probe of claim 1 wherein the ultrasonic transducer comprises a first ultrasonic transducer, wherein the transducer shaft further comprises a second ultrasonic transducer disposed at the distal end portion diametrically opposed to the first ultrasonic transducer, and wherein the transducer housing conforms to the second ultrasonic transducer.

12. The rotational intravascular ultrasound probe of claim 1 wherein the ultrasonic transducer comprises a first ultrasonic transducer, wherein the transducer shaft further comprises a second ultrasonic transducer and a third ultrasonic transducer disposed at the distal end portion, wherein the first ultrasonic transducer, the second ultrasonic transducer, and the third ultrasonic transducer are circumferentially positioned 120° from one another, and wherein the transducer housing conforms to the second ultrasonic transducer and the third ultrasonic transducer.

13. The rotational intravascular ultrasound probe of claim 1 wherein the transducer shaft further comprises an electrical wire of the plurality of electrical wires in communication with the ultrasonic transducer and extending from the proximal end portion to the distal end portion, wherein a proximal portion of the electrical wire is disposed within the drive cable, and wherein the transducer housing surrounds a distal portion of the electrical wire.

14. The rotational intravascular ultrasound probe of claim 1 wherein the transducer housing comprises one or more of loaded plastic and epoxy.

15. The rotational intravascular ultrasound probe of claim 1, wherein the transducer housing conforms to and physically contacts side surfaces of the ultrasonic transducer.

16. The rotational intravascular ultrasound probe of claim 1, wherein the transducer housing conforms to and physically contacts an entire back surface of the ultrasonic transducer.

17. The rotational intravascular ultrasound probe of claim 1, wherein the transducer housing completely surrounds the distal portion of the drive cable and partially surrounds the ultrasonic transducer.

18. The rotational intravascular ultrasound probe of claim 1, wherein the transducer housing conforms to and physically contacts a longitudinal portion of the plurality of electrical wires extending between the distal portion of the drive cable and the ultrasonic transducer.

19. The rotational intravascular ultrasound probe of claim 1, wherein the transducer housing conforms to and physically contacts a first side surface, an opposite second side surface, and an entire back surface of the ultrasonic transducer.

* * * * *